(12) United States Patent
Chong et al.

(10) Patent No.: US 7,413,560 B2
(45) Date of Patent: Aug. 19, 2008

(54) SAFETY ARTERIOVENOUS FISTULA NEEDLE

(75) Inventors: Swee Cheau Chong, Hayward, CA (US); Yasushi Takigawa, Moraga, CA (US)

(73) Assignee: JMS North America Corporation, Hayward, CA (US)

( * ) Notice: Subject to any disclaimer, the term of this patent is extended or adjusted under 35 U.S.C. 154(b) by 240 days.

(21) Appl. No.: 10/824,815

(22) Filed: Apr. 15, 2004

(65) Prior Publication Data
US 2005/0234408 A1    Oct. 20, 2005

(51) Int. Cl.
*A61M 5/32* (2006.01)
(52) U.S. Cl. ........................ 604/174; 604/171; 604/177; 604/198; 604/158; 604/164
(58) Field of Classification Search ................. 604/171, 604/177, 198, 174, 175, 158, 164
See application file for complete search history.

(56) References Cited

U.S. PATENT DOCUMENTS 5,779,679 A * 7/1998 Shaw .......................... 604/158
5,931,815 A * 8/1999 Liu ............................. 604/171

* cited by examiner

*Primary Examiner*—Kevin C. Srmons
*Assistant Examiner*—Phillip Gray
(74) *Attorney, Agent, or Firm*—Pillsbury Winthrop Shaw Pittman LLP (57) ABSTRACT

A Safety Arteriovenous Fistula (AVF) winged safety needle device provides a safety feature including a protective shield with handling wings, which when placed in cooperating relationship, allows accommodation of a blood collection needle and a hub. The Safety AVF provides a reliable and user friendly first releasable locking mechanism in an insertion position and a second unreleaseable locking mechanism in a protected position. The Safety AVF also allows for rotation of the needle after cannulation in order to maximize blood or fluid flow to or from a vessel.

23 Claims, 8 Drawing Sheets

SAFETY ARTERIOVENOUS FISTULA NEEDLE

BACKGROUND OF THE INVENTION

1. Field of the Invention

The present invention relates to a winged safety needle assembly and, more particularly, to a winged safety needle assembly having a winged cylindrical sheath for substantially reducing sticking accidents from taking place when retracting the needle into the winged cylindrical sheath. Protection of the edge of the needle is achieved by unlocking and sliding the needle along the inner wall of the winged cylindrical sheath.

2. Discussion of the Related Art

Proper disposal of used needles is required to avoid needlestick injuries. Used needles may be recapped with the same cover that originally covered the needles before use or by similar covers or tubes before the needle is discarded. This method requires movement of the hands toward the exposed needle and may promote needlestick injuries during the recapping. In addition, needles may also be disposed of by tossing them into nearby refuse containers. However, this creates danger to those who handle the refuse containers.

Figure 8A:
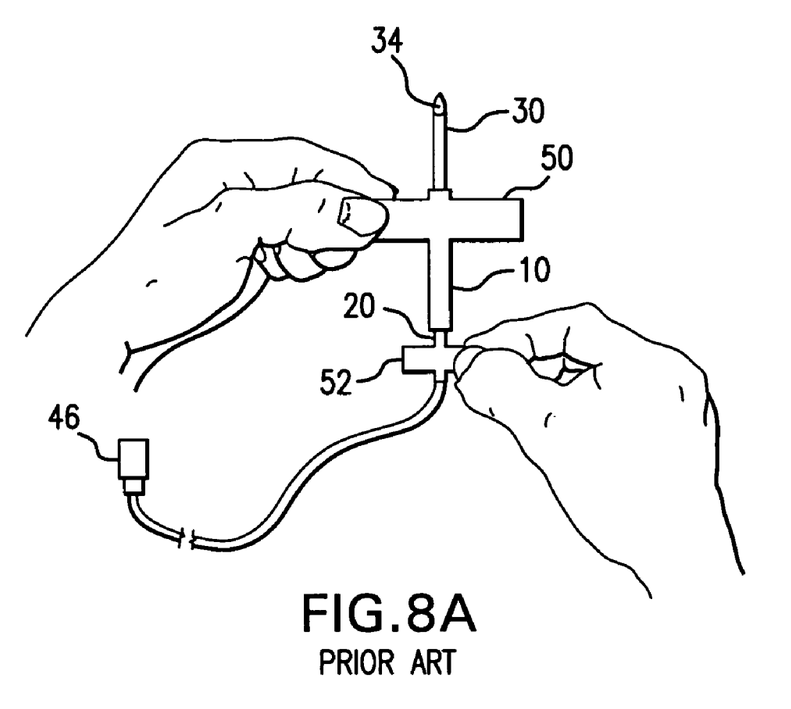
FIG. 8a illustrates a prior art intravenous butterfly needle.
Figure 8B:
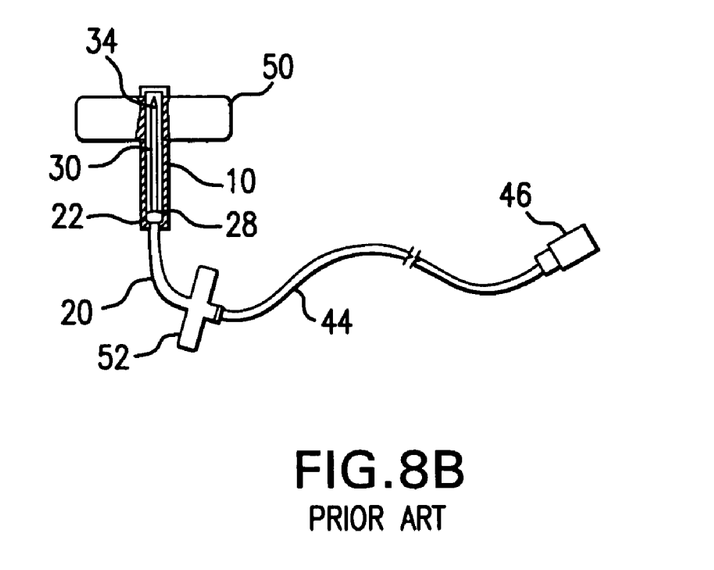
FIG. 8b illustrates a prior art intravenous butterfly needle.

Winged intravenous (IV) sets are well known in the art. A typical prior art IV butterfly needle used for the insertion into blood vessels and similar passageways in the body to permit the infusion or withdrawal of sterile fluids or blood is illustrated in FIG. 8a and FIG. 8b. The butterfly needle generally has a hollow needle or cannula 30, a cylindrical hub 20 holding the needle 30 at one end and connected to an IV tube 52 at the opposite end, and a cylindrical housing 10 surrounding the needle with a wing-like extension 50 extending on each side thereof.

The wings 50 are used to handle the assembly during insertion and withdrawal. For example, the wings of the needle assembly may be folded upwards around the hub to provide a gripping extension for the technician or nurse to use when attempting to insert the needle into the desired vein, artery or other passageway. The wings are also used to stabilize the device while in place by providing a broad surface area of contact with the patient which allows for taping of the device to the patient while discouraging movement, especially rotation, of the device. This assists the technician or nurse in affixing the needle to the patient during the infusion of fluids or medicants.

A problem typical of butterfly needles as just described is that when the needle is withdrawn from the vein or artery, the sharpened end, now contaminated with blood or other body fluid, remains exposed. The exposed needle can be a source of great danger to the operator or to anyone who might be pricked or scratched. Needle injuries may result in the transmission of diseases such as hepatitis, HIV, or cause other types of infection. A common solution available to the operator was to simply drop the needle and the holder into a trash receptacle. However, a danger to clean up and medical waste disposal personnel continues if the used needles are not rendered harmless in some way. Another solution is to attempt to recap the needle with a safety cover immediately after use. This, however, may in itself cause injury if the operator should accidentally stick themselves during the recapping process. In addition, caps or covers may come loose and expose the used needle.

Therefore, in order to substantially reduce such sticking accidents various proposals have been made. One such proposal is a winged needle assembly disclosed in U.S. Pat. No. 5,505,711 (hereinafter referred to as the '711 patent). The '711 patent describes an indwelling injector needle assembly having wings including a cannula or needle body, a hub supporting a proximal end of the needle body, a tube in fluid communication with the needle body, a cylindrical holder having a distal end from which the wings protrude, and a latching mechanism. The hub can slide along an inner periphery of the holder between a first position near the distal end of the holder and a second position near a proximal end of the holder. The latching mechanism is formed in and disposed between the hub and the holder so that the hub is inhibited from moving from the first position toward the second position, and vice versa. The needle edge can be retracted within the holder while the wings remain fixed to a patient's skin.

However, the winged needle assembly disclosed in the '711 patent has a key disadvantage. The '711 patent discloses a structure that includes a non-rotating needle. A rotatable needle is preferable in order to maximize blood or fluid flow to or from a vessel in which the needle is inserted. The structure of the '711 patent prevents the needle from being rotated after cannulation. The '711 patent also describes a hub supporting the non-rotating needle. The hub has a guide groove formed in a peripheral wall thereof, the groove extending longitudinally of the hub. A cylindrical holder having wings is disposed on the hub. The cylindrical holder has a lug protruding inwardly from an inner peripheral surface of a proximal end thereof. The lug is slidably engaged with the guide groove in the hub so that the hub can be moved relative to the holder between a first position in which the needle body protrudes from a distal end of the cylindrical holder and a second position in which the needle body is retracted so that a pricking edge of the needle body is within the holder. The needle and hub cannot rotate relative to the cylindrical holder due to the lug being slidably engaged with the guide groove in the hub. Therefore the needle cannot be rotated when needed after cannulation in order to maximize blood or fluid flow to or from the vessel.

As can be seen, what is needed is a winged safety needle device that allows for rotation of the needle after cannulation in order to maximize blood or fluid flow to or from the vessel, and provides for a reliable and user friendly first releasable locking mechanism in an insertion position and a second unreleaseable locking mechanism in a protected position.

DETAILED DESCRIPTION

Figure 1:
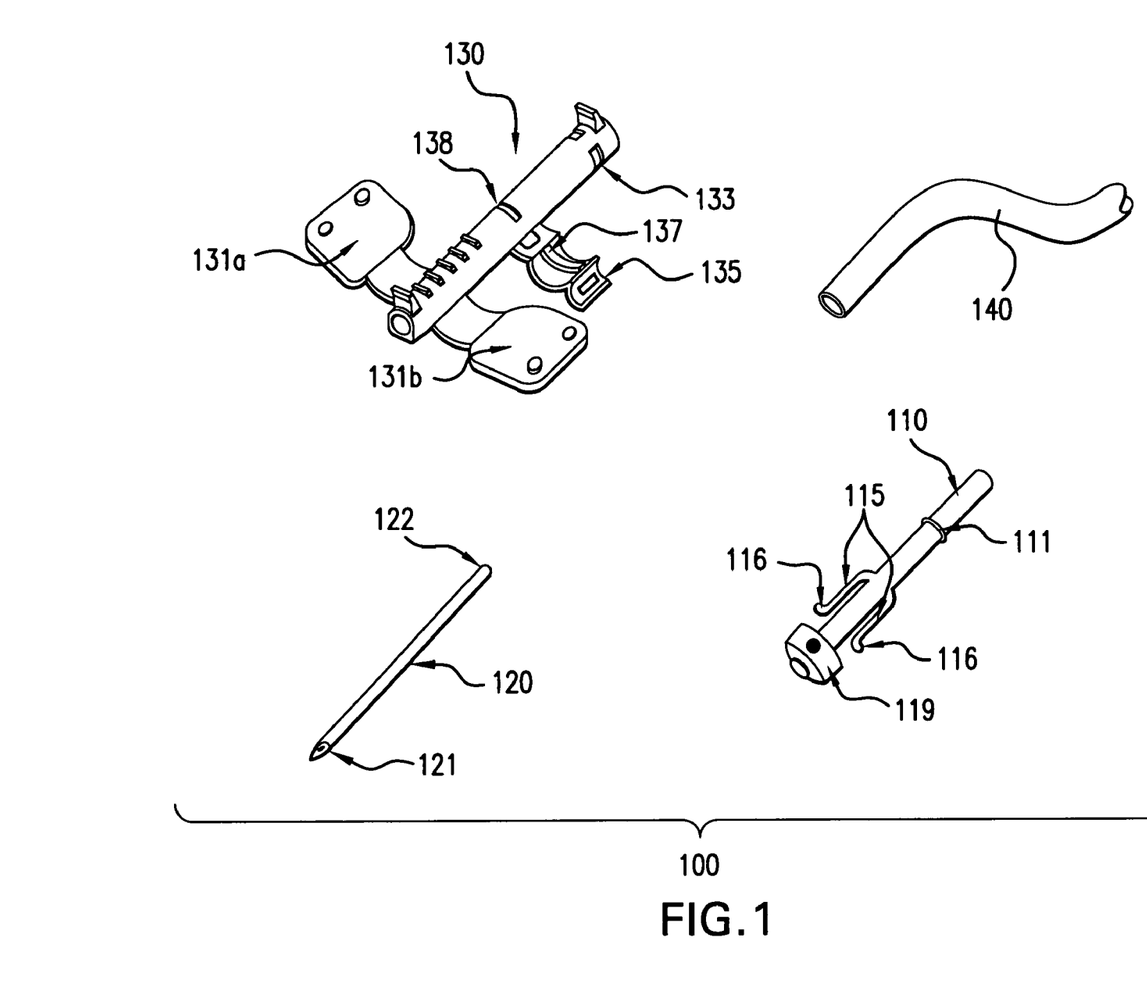
FIG. 1 illustrates an exploded view of the Safety AVF needle according to an embodiment of the present invention.
Figure 3A:
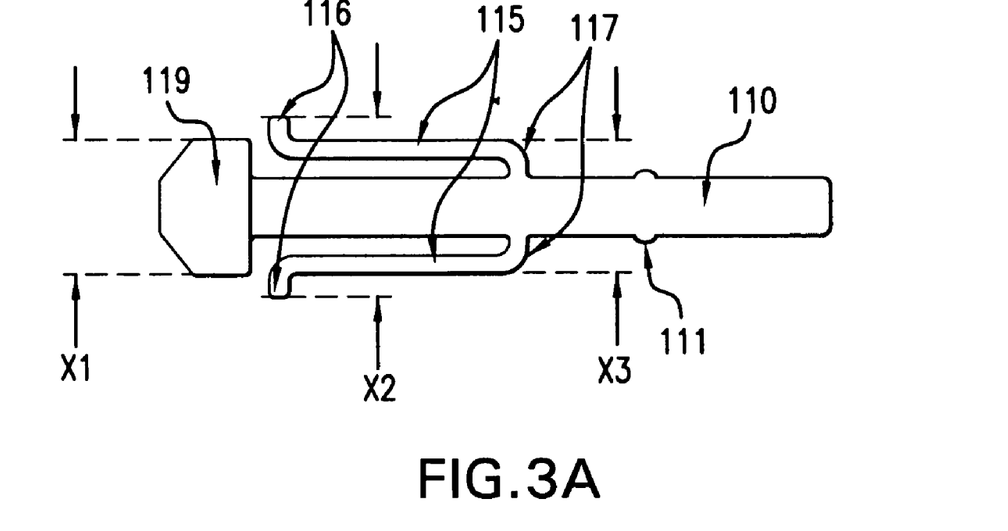
FIG. 3a illustrates a PC hub with a pair of flexible extension arms in a pre-assembled state according to an embodiment of the present invention.
Figure 3B:
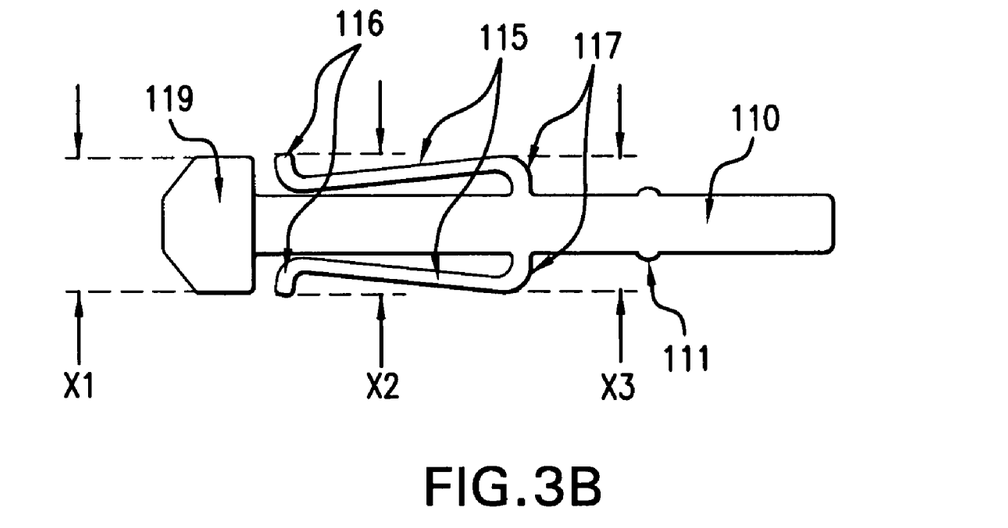
FIG. 3b illustrates a PC hub with a pair of flexible extension arms in an assembled state according to an embodiment of the present invention.

The Safety Arteriovenous Fistula (AVF) needle assembly 100 as shown in FIG. 1, is a retractable winged safety needle device having a needle holder 110 (referred to as a polycarbonate (PC) hub), a needle or cannula 120, and a winged sheath 130. Referring to FIGS. 1, 3a, and 3b the PC hub 110 is tubular, may be made of a polycarbonate material, and holds a proximal end of the needle or cannula 120 at the distal end. The needle or cannula 120 is hollow and has a beveled edge 121 at the distal end. The base 122 or proximal portion of the hollow needle 120 is fixed to and supported by a conical shaped head 119 of the PC hub 110. A polyvinyl chloride (PVC) tube 140 for use in fluid administration is slid over the proximal end of the PC hub 110, providing a fluid tight seal.

The PC hub 110 has the conical shaped head 119 at the distal end and a stopper 111 at the proximal end for tube 140 bonding. Furthermore, the PC hub 110 has a pair of flexible extension arms 115 located approximately in the center of the PC hub 110 and extending toward the conical shaped head 119 at the distal end that serve as a key component to provide for a first releasable locking mechanism and a second unreleaseable locking mechanism. The conical shaped head 119 serves to stabilize the PC hub 110 and the needle 120 during a cannulation procedure.

Referring to FIG. 3a, the PC hub 110 including the conical shaped head 119 and the pair of flexible extension arms 115 is shown in a pre-assembled state, i.e., before insertion into the winged sheath 130. A cross-sectional width (X2) of the tips 116 of the flexible extension arms is greater than a cross-sectional width (X1) of the conical shaped head 119 and a cross-sectional width (X3) of a proximal portion 117 of the flexible extension arms 115 such that X2>X1>X3. The cross-sectional width (X3) of the proximal portion 117 of the flexible extension arms 115 being less than the cross-sectional width (X1) of the conical shaped head 119 allows for a smooth needle retraction.

Referring to FIG. 3b, the PC hub 110 including the conical shaped head 119 and the pair of flexible extension arms 115 is shown in an assembled state, i.e., after insertion into the winged sheath 130. A cross-sectional width (X2) of the tips 116 of the flexible extension arms may remain greater than or equal to a cross-sectional width (X1) of the conical shaped head 119 and a cross-sectional width (X3) of the proximal portion 117 of the flexible extension arms 115 such that X2≧X1>X3. Also shown, a gap (G1) may remain between a base of the tips 116 of the flexible extension arms and the PC hub 110 when the flexible extension arms 115 are flexed inward in the assembled state. The gap (G1) also allows for a smooth needle retraction.

Figure 2:
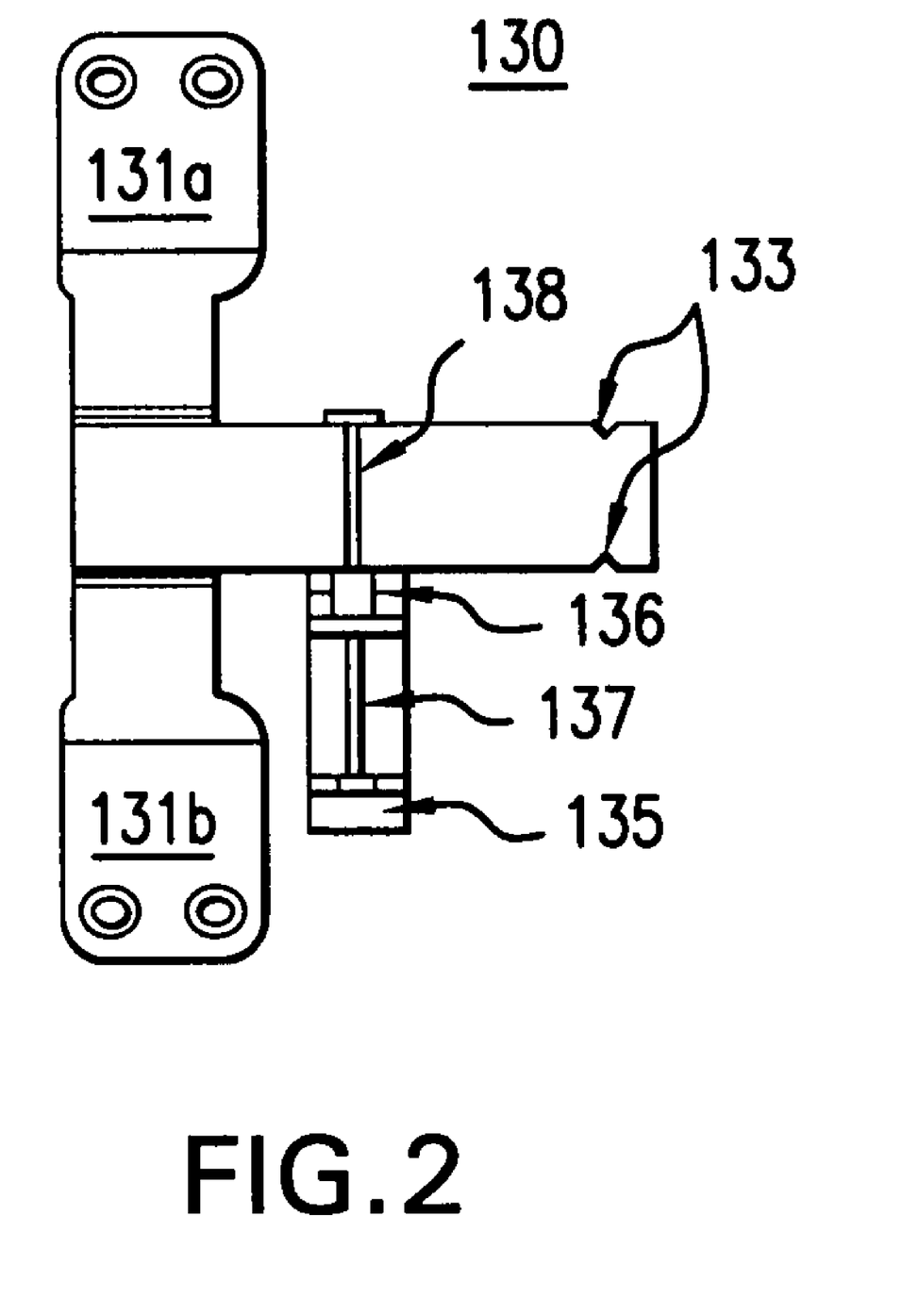
FIG. 2 illustrates a winged sheath according to an embodiment of the present invention.
Figure 4:
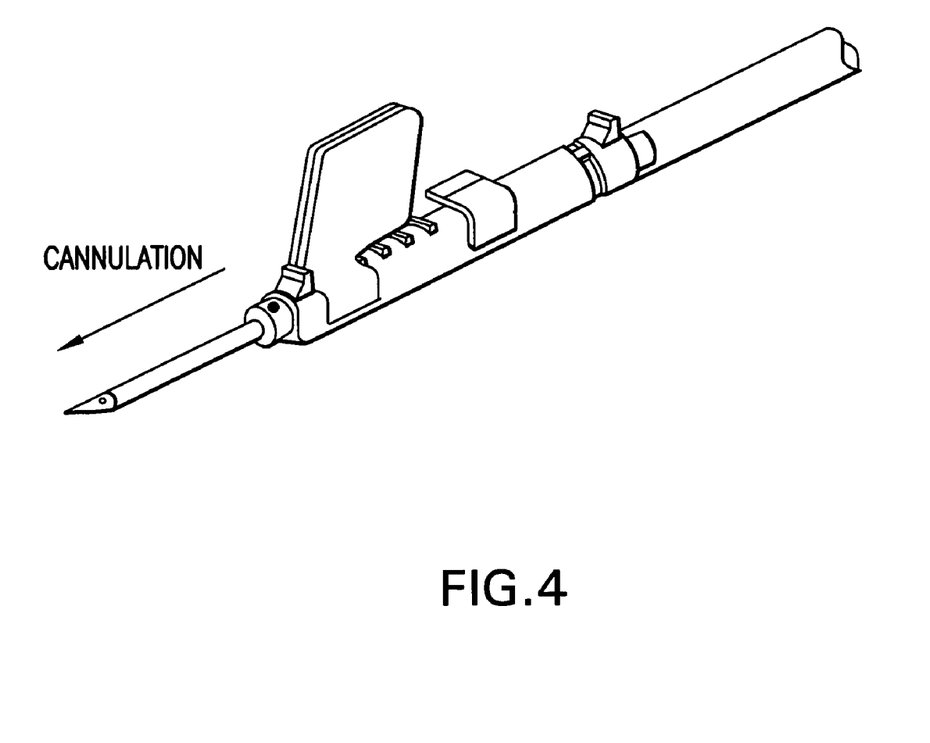
FIG. 4 illustrates a cannulation procedure of the Safety AVF needle according to an embodiment of the present invention.
Figure 5:
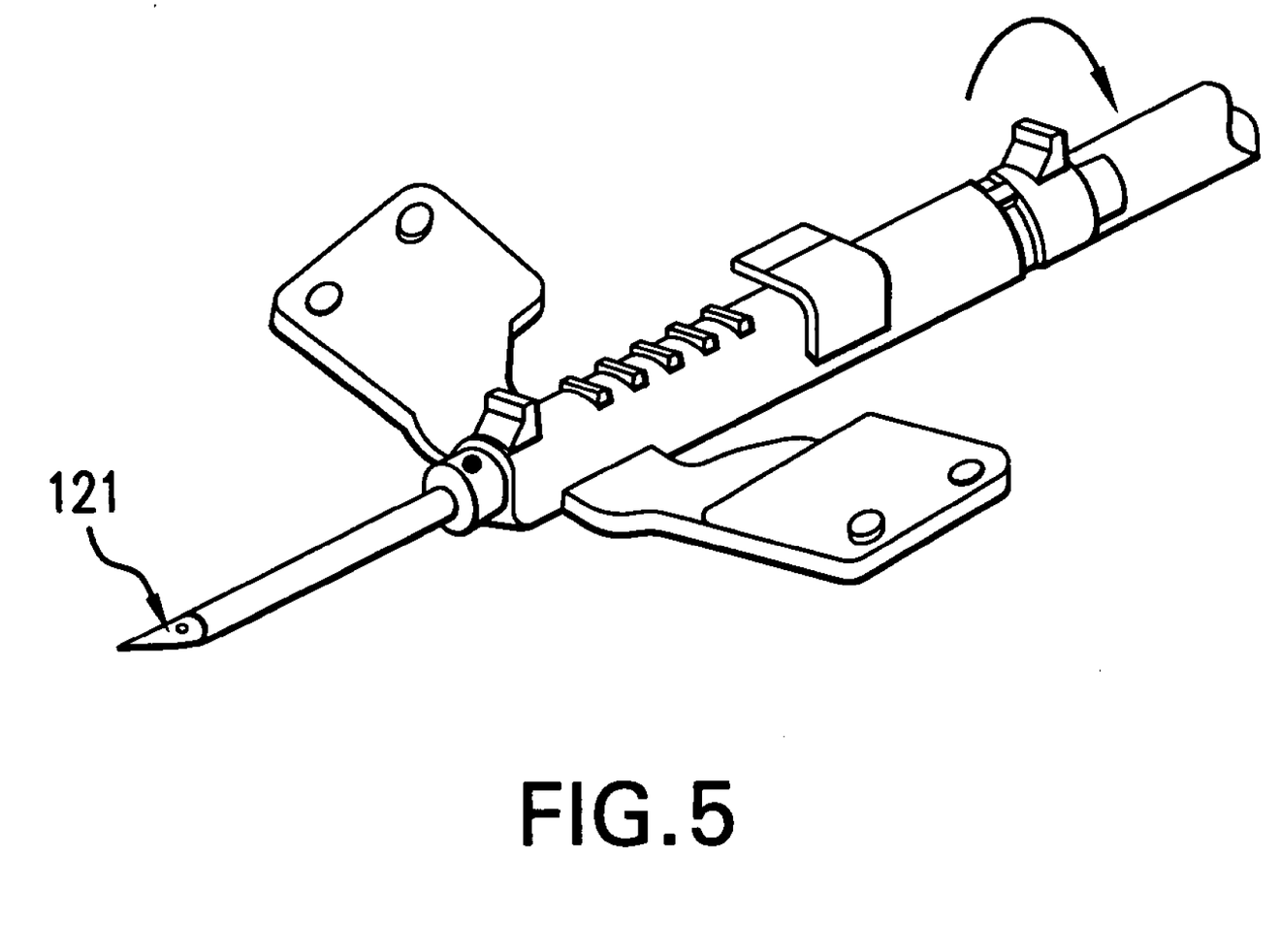
FIG. 5 illustrates a view showing an orientation of a cannula bevel according to an embodiment of the present invention.
Figure 6:
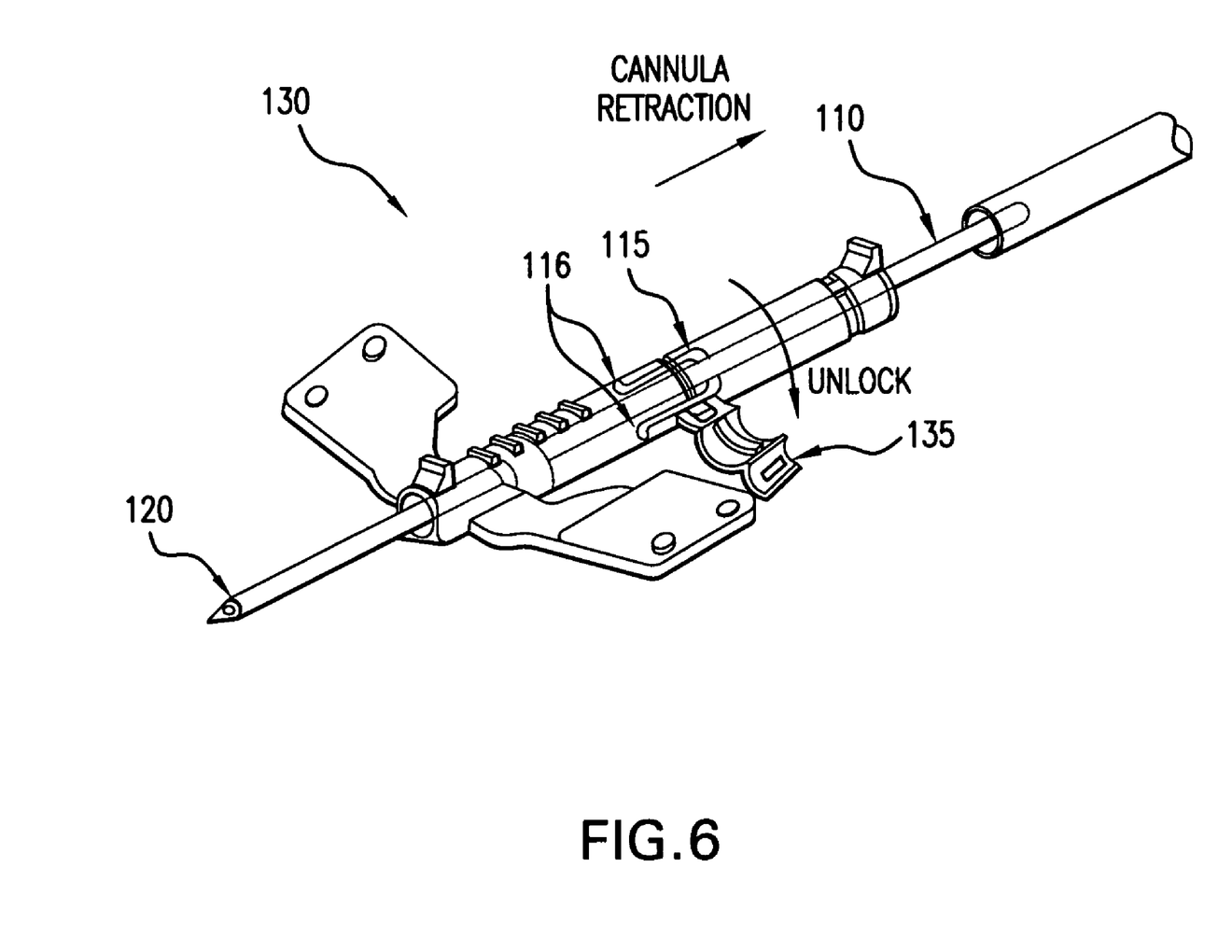
FIG. 6 illustrates a retraction procedure of the Safety AVF needle according to an embodiment of the present invention.

Referring to FIG. 2, the winged sheath 130 is a cylindrical structure with a hollow interior. The winged sheath 130 may be made of a polymeric material such as a polyethylene, or any other suitable material. The winged sheath 130 is axially slideable on the PC hub 110 and may have a constant inner diameter (defining the hollow interior). At the distal end of the sheath, a pair of wings 131a, 131b are positioned for use in grasping the device when squeezed together (see also FIG. 4) and for adhering the device to a patient's skin during infusion, haemodialysis, apheresis, and blood collection when laying flat (see also FIG. 5). The flexible wings 131a, 131b, may be integrally formed with the body of the supporting cylinder of the winged sheath 130 on both sides thereof, and the shape of the wings 131a, 131b, is not particularly limited. The wings 131a, 131b are preferably provided on the cylinder body to form one plane as shown in FIG. 1, FIG. 2, and FIG. 5.

The first releasable locking mechanism will now be described according to embodiments of the present invention. Referring to FIG. 2, FIG. 3a, FIG. 3b, and FIGS. 7a-7d the winged sheath 130 may have a front linear groove 132 located on the interior surface at the distal end that may accept the tips 116 of the flexible extension arms 115 of the PC hub 110, may allow for 360 degree rotation of the PC hub 110 with the attached extension arms 115 within the winged sheath 130, and may function as part of the first releasable locking mechanism. The flexible extension arms 115 of the PC hub 110 partially spring outward allowing the tips 116 of the flexible arms 115 to releasably seat in the front linear groove 132 (see FIG. 7a).

Alternative embodiments of the present invention may achieve 360 degree rotation of the PC hub 110 with the attached extension arms 115 within the winged sheath 130 without the use of a front linear groove 132 located on the interior surface. In such an embodiment the absence of a front linear groove 132 would prevent the tips 116 of the flexible extension arms 115 from partially springing outward and functioning as part of the first releasable locking mechanism.

Alternative embodiments of the present invention may include an inner circumferential rib 141 provided at the inner distal surface of the winged sheath 130. The inner circumferential rib 141 in combination with a locking tab 130 described below may functioning as part of the first releasable locking mechanism.

The locking tab 135 with a projection 137 located at approximately the center of the winged sheath can be selectively placed in a locked or unlocked position. The locking tab 135 is attached to the side of the winged sheath 130 by a hinge 136 so that when in an unlocked position, it remains attached thereto. In the locked position the projection 137 of the locking tab 135 fits into a slot 138 in the winged sheath 130. The projection 137 extends through the slot 138 into the hollow interior portion of the winged sheath 130 to abut against the proximal portion 117 of the flexible extension arms 115 of the PC hub 110 to prevent retraction of the PC hub 110 with needle or cannula 120 with respect to the winged sheath 130. The projection 137 of the locking tab 135 will cover at least 180 degrees or half of the inner circumferential diameter of the winged sheath 130 to abut against the proximal portion 117 of the flexible extension arms 115 (see FIGS. 7a, 7b, 7c).

The first locking mechanism may consist of the locking tab 135 with the projection 137 abutting against the proximal portion 117 of the flexible extension arms 115 in conjunction with the tips 116 of the flexible arms 115 releasably seating in the front linear groove 132. In an alternative embodiment of the present invention, the first locking mechanism may consist of the locking tab 135 with the projection 137 abutting against the proximal portion 117 of the flexible extension arms 115 in conjunction with the tips 116 of the flexible arms 115 abutting against the inner circumferential rib 141 provided at the inner distal surface of the winged sheath 130.

Referring to FIG. 5, the Safety AVF needle assembly 100 also includes a rotational feature that allows the PC hub 110 with attached needle or cannula 120 to rotate 360 degrees within the winged sheath 130. This feature allows the cannula bevel 121 orientation within the fistula or graft to be ascertained and adjusted.

In an embodiment of the present invention, the winged sheath 130 having front linear groove 132 located on the interior surface at the distal end accepts the tips 116 of the flexible extension arms 115 of the PC hub 110, and allows for 360 degree rotation of the PC hub 110 with the flexible extension arms 115 within the winged sheath 130. A black dot may be stamped or marked on the distal exterior surface of the conical surface 119 of the hub 110 and is visible from above when facing up (see FIG. 5) to indicate the cannula bevel 121 is facing up within the fistula or graft. Alternatively, a red dot may be stamped or marked on the distal exterior surface of the conical surface 119 of the hub 110 and is visible from above when facing up (not visible as shown in FIG. 5) to indicate the cannula bevel 121 is facing down within the fistula or graft. This mechanism allows the handling of the Safety AVF needle assembly 100 of the present invention to be simplified. For example, after inserting the needle 120 with the beveled surface 121 facing up into a blood vessel (the black dot on the distal exterior surface of the conical surface 119 of the hub 110 is visible when facing up as shown in FIG. 5), the beveled edge 121 may be made to face down by simply rotating the hub 110 until the red dot on the distal exterior surface of the conical surface 119 of the hub 110 is visible when facing up. The needle 120 may then be retained in that state (not shown in FIG. 5). The ability to adjust the orientation (0-360 degrees) of the cannula bevel 121 within a vessel allows a technician to adjust for maximum fluid flow. For example, due to the various shapes and sizes of blood vessels, direction of fluid flows, and other particularities, etc., it is beneficial to be able to rotate the cannula 120 to maximize flow.

In contrast, some prior art winged retention needles have the disadvantage that the rotational operation thereof is troublesome. An assembly with a hollow needle directly affixed to a winged portion requires the entire assembly, needle and wings, to be rotated as one. For example, if a bevel edge surface is facing up upon insertion into a blood vessel, the entire winged needle assembly would need to be rotated by a half rotation so that the bevel edge surface would be faced down. If the wings have been previously secured to the patient with tape, the tape would have to be removed prior to rotation.

The second releasable locking mechanism will now be described according to embodiments of the present invention. Referring to FIG. 2, FIG. 3a, FIG. 3b, and FIGS. 7a-7d the winged sheath 130 has a slot 133 located through the interior/exterior surface and extending ⅔ of the circumference of the proximal end of the winged sheath 130. The slot 133 may accept the tips 116 of the flexible extension arms 115 of the PC hub 110 to provide for the second unreleaseable locking mechanism. The flexible extension arms 115 of the PC hub 110 fully spring outward allowing the tips 11 6to unreleasably seat in the slot 133 (see view 7d).

In addition, an inner circumferential rib 139 is provided at the inner proximal surface of the winged sheath 130. The inner circumferential rib 139 abuts against the tips 116 of the flexible extension arms 115 in the second unreleaseable (final) locked position to prevent the PC hub 110 from being pulled out of the winged sheath 130. Referring to FIG. 3b, the inner diameter of the inner circumferential rib 139 may be larger than the width X3 and smaller than the width X2. This allows for smooth retraction of the PC hub 110 into the winged sheath 130. Otherwise the base 117 of the flexible extension arms 115 will abut against the inner circumferential rib 139, the needle 120 may not be retracted within the winged sheath 130, and the tips 116 of the flexible arm 115 may not seat into the slot 133.

Figure 7A:
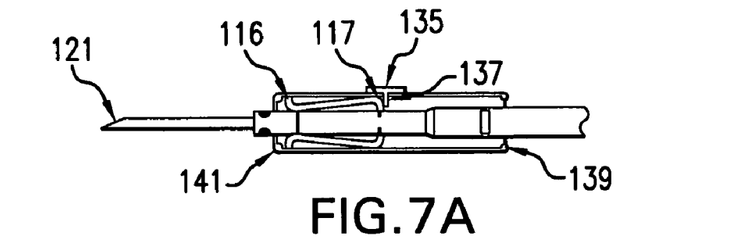
FIG. 7a illustrates a side view of the Safety AVF needle according to an embodiment of the present invention.
Figure 7B:
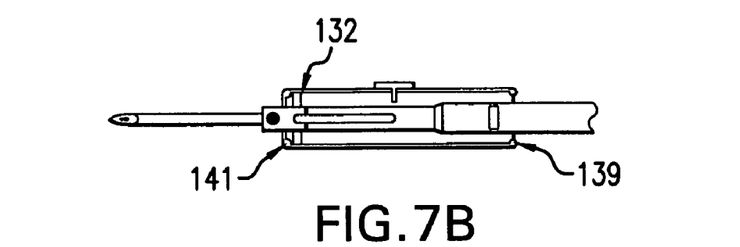
FIG. 7b illustrates a side view of the Safety AVF needle according to an embodiment of the present invention.
Figure 7C:
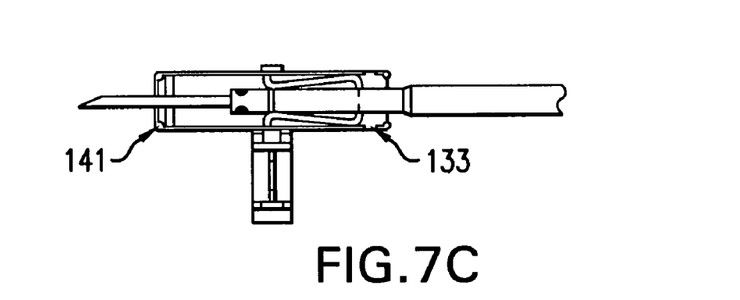
FIG. 7c illustrates a top view of the Safety AVF needle according to an embodiment of the present invention.
Figure 7D:
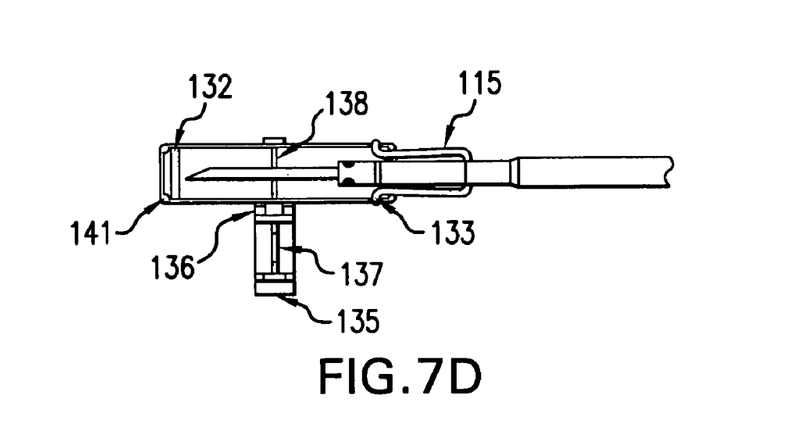
FIG. 7d illustrates a top view of the Safety AVF needle according to an embodiment of the present invention.

It should be noted that a width (W1) of the slot 138 in the winged sheath 130 that accommodates the projection 137 from the locking tab 135 is smaller than a width (W2) of the slot 133 located at the proximal end of the winged sheath 130 to prevent the tips 116 of the flexible extension arms 115 from seating in the W1 slot 138 (width of W1 and W2 are not shown, see view 7d for view of tips 116 seating in slot 133).

Operation of the Safety AVF needle 100 will now be described according to embodiments of the present invention. In the insertion position, the needle 120 is exposed through the distal end of the sheath 130 and may be held in this position according to two mechanisms. First, the flexible extension arms 115 of the PC hub 110 partially spring outward allowing the tips 116 to releasably seat in the front linear groove 132 when the PC hub 110 is pushed to the distal end of the sheath 130, and second, the projection 137 of the locking tab 135 abuts against the proximal portion 117 of the flexible extension arms 115.

Referring to FIG. 6 and FIGS. 7a-7d, when the needle 120 is to be withdrawn, the locking tab 135 is disengaged and the PC hub 110/needle 120 are pulled in a proximal direction (releasing the tips 116 of the extension arms 115 from the front groove 132). PC hub 110/needle 120 are drawn proximally until the tips 116 of the flexible extension arms 115 are pulled to the proximal end of the sheath 130 wherein the tips 116 will fully spring outward and unreleasably seat in the slot 133. It should be noted that the locking tab 135 is used only for maintaining the locked relationship between the sheath 130 and PC hub 110 in the insertion position (see view 7a and view 7b) and not in the protection position (see view 7d).

While the description above refers to particular embodiments of the present invention, it will be understood that many modifications may be made without departing from the spirit thereof. The accompanying claims are intended to cover such modifications as would fall within the true scope and spirit of the present invention. The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A winged safety needle assembly, comprising:
    a hub having a distal end, a proximal end, and an axial through hole, said hub further supporting a pair of flexible extension arms, said pair of flexible extension arms each having a shoulder that extends from said hub at approximately a center of said hub, said pair of flexible extension arms extending toward the distal end of the hub;
    a cannula joined to said hub adjacent the distal end of said hub, said cannula having a beveled edge at a distal end thereof;
    a cylindrical sheath having a locking tab attached to an outer surface thereof by a hinge, said locking tab being rotatable over at least a 180 degree arc, said cylindrical sheath retaining said hub therein and having a distal end and a proximal end, said hub being slideable along an inner surface of said cylindrical sheath from a first position at which the distal end of said cannula joined to said hub projects beyond the distal end of said cylindrical sheath by a predetermined length, to a second position at which said distal end of the cannula is protectively contained within said cylindrical sheath;
    a pair of flexible wings provided on the outer peripheral surface adjacent the distal end of said cylindrical sheath; and a first locking mechanism and a second locking mechanism disposed on said assembly, said first locking mechanism releasably locking said hub and said cylindrical sheath at the first position, and said second locking mechanism unreleasably locking said hub and said cylindrical sheath at the second position, wherein said first locking mechanism comprises said pair of flexible extension arms supported by said hub and a groove formed on the inner surface of the distal end of said cylindrical sheath in combination with said locking tab and a slot in the cylindrical sheath, and when said hub is locked at the first position in relation to said cylindrical sheath a pair of tips of said pair of flexible extension arms releasably engages the groove, and said locking tab includes an arc shaped projection that is inserted through the slot in the cylindrical sheath to directly engage the shoulders of the pair of flexible extension arms, said arc shaped projection having an arc length that extends over a 180 degree arc.

2. A winged safety needle assembly according to claim 1, wherein said second locking mechanism comprises said pair of flexible extension arms supported by said hub and a pair of slots formed in the proximal end of said cylindrical sheath, wherein when said hub is at the second position in relation to said cylindrical sheath the pair of tips of said pair of flexible extension arms unreleasably engages said pair of slots.

3. A winged needle assembly according to claim 1, wherein said cannula is axially rotatable relative to the cylindrical sheath.

4. A winged needle assembly according to claim 1, wherein said hub is marked to indicate an orientation of the bevel edge of the cannula relative to the cylindrical sheath.

5. A winged needle assembly according to claim 4, wherein a width of the pair of slots is greater than a width of the slot in the cylindrical sheath.

6. A winged needle assembly according to claim 1, wherein a tube is connected to the proximal end of the hub.

7. A winged needle assembly according to claim 2, wherein an inner circumferential rib is provided on the interior proximal end of said cylindrical sleeve to abut against the pair of tips of said pair of flexible extension arms.

8. A winged needle assembly according to claim 1, wherein an inner circumferential rib is provided on the interior distal end of said cylindrical sleeve to abut against the pair of tips of said pair of flexible extension arms.

9. A winged safety needle assembly, comprising:
a hub having a distal end, a proximal end, and an axial through hole, said hub further supporting a pair of flexible extension arms, said pair of flexible extension arms each having a shoulder that extends from said hub at approximately a center of said hub, said pair of flexible extension arms extending toward the distal end of the hub;
a cannula joined to said hub adjacent the distal end of said hub, said cannula having a beveled edge at a distal end thereof;
a cylindrical sheath having a locking tab attached to an outer surface thereof by a hinge, said locking tab being rotatable over at least a 180 degree arc, said cylindrical sheath retaining said hub therein and having a distal end and a proximal end, said hub being slideable along an inner surface of said cylindrical sheath from a first position at which the distal end of said cannula joined to said hub projects beyond the distal end of said cylindrical sheath by a predetermined length, to a second position at which said distal end of the cannula is protectively contained within said cylindrical sheath, wherein said cannula joined to said hub is axially rotatable relative to said cylindrical sheath at said first position;
a pair of flexible wings provided on the outer peripheral surface adjacent the distal end of said cylindrical sheath; and
a first locking mechanism and a second locking mechanism disposed on said assembly, said first locking mechanism releasably locking said hub and said cylindrical sheath at the first position, and said second locking mechanism unreleasably locking said hub and said cylindrical sheath at the second position, wherein said first locking mechanism comprises said pair of flexible extension arms supported by said hub and a groove formed on the inner surface of the distal end of said cylindrical sheath in combination with said locking tab and a slot in the cylindrical sheath, and when said hub is locked at the first position in relation to said cylindrical sheath a pair of tips of said pair of flexible extension arms releasably engages the groove, and said locking tab includes a projection that is inserted through the slot in the cylindrical sheath to directly engage the shoulders of the pair of flexible extension arms, said cannula joined to said hub being axially rotatable relative to said cylindrical sheath at said locked first position.

10. A winged safety needle assembly according to claim 9, wherein said second locking mechanism comprises said pair of flexible extension arms supported by said hub and a pair of slots formed in the proximal end of said cylindrical sheath, wherein when said hub is at the second position in relation to said cylindrical sheath the pair of tips of said pair of flexible extension arms unreleasably engages said pair of slots.

11. A winged needle assembly according to claim 9, wherein said hub is marked to indicate an orientation of the bevel edge of the cannula relative to the cylindrical sheath.

12. A winged needle assembly according to claim 9, wherein a width of the pair of slots is greater than a width of the slot in the cylindrical sheath.

13. A winged needle assembly according to claim 9, wherein a tube is connected to the proximal end of the hub.

14. A winged needle assembly according to claim 10, wherein an inner circumferential rib is provided on the interior proximal end of said cylindrical sleeve to abut against the pair of tips of said pair of flexible extension arms.

15. A winged needle assembly according to claim 9, wherein an inner circumferential rib is provided on the interior distal end of said cylindrical sleeve to abut against the pair of tips of said pair of flexible extension arms.

16. A winged safety needle assembly, comprising:
a hub having a conical shaped head at a distal end thereof larger in diameter than a proximal end of said hub, said hub further supporting a pair of flexible extension arms, said pair of flexible extension arms each having a shoulder that extends from said hub at approximately a center of said hub, said pair of flexible extension arms extending toward the distal end of the hub;
a cannula joined to said conical shaped head at the distal end of said hub, said cannula having a beveled edge at a distal end thereof;
a cylindrical sheath having a locking tab attached to an outer surface thereof by a hinge, said locking tab being rotatable over at least a 180 degree arc, said cylindrical sheath retaining said hub therein and having a distal end and a proximal end, said hub being slideable along an inner surface of said cylindrical sheath from a first position at which the distal end of said cannula joined to said hub projects beyond the distal end of said cylindrical sheath by a predetermined length, to a second position at which said distal end of the cannula is protectively contained within said cylindrical sheath, wherein said cannula joined to said conical shaped head both being axially rotateable relative to said cylindrical sheath at said first position;

a pair of flexible wings provided on the outer peripheral surface adjacent the distal end of said cylindrical sheath; and a first locking mechanism and a second locking mechanism disposed on said assembly, said first locking mechanism releasably locking said hub and said cylindrical sheath at the first position, and said second locking mechanism unreleasably locking said hub and said cylindrical sheath at the second position, wherein said first locking mechanism comprises said pair of flexible extension arms supported by said hub and a groove formed on the inner surface of the distal end of said cylindrical sheath in combination with said locking tab and a slot in the cylindrical sheath, and when said hub is locked at the first position in relation to said cylindrical sheath a pair of tips of said pair of flexible extension arms releasably engages the groove, and said locking tab includes a projection that is inserted through the slot in the cylindrical sheath to directly engage the shoulders of the pair of flexible extension arms.

17. A winged safety needle assembly according to claim 16, wherein said second locking mechanism comprises said pair of flexible extension arms supported by said hub and a pair of slots formed in the proximal end of said cylindrical sheath, wherein when said hub is at the second position in relation to said cylindrical sheath the pair of tips of said pair of flexible extension arms unreleasably engages said pair of slots.

18. A winged needle assembly according to claim 16, wherein said conical shaped head is marked to indicate an orientation of the bevel edge of the cannula relative to the cylindrical sheath.

19. A winged needle assembly according to claim 16, wherein a width of the pair of slots is greater than a width of the slot in the cylindrical sheath.

20. A winged needle assembly according to claim 16, wherein a tube is connected to the proximal end of the hub.

21. A winged needle assembly according to claim 17, wherein an inner circumferential rib is provided on the interior proximal end of said cylindrical sleeve to abut against the pair of tips of said pair of flexible extension arms.

22. A winged needle assembly according to claim 16, wherein an inner circumferential rib is provided on the interior distal end of said cylindrical sleeve to abut against the pair of tips of said pair of flexible extension arms.

23. A winged needle assembly according to claim 16, wherein said locking tab includes an arc shaped projection having an arc length that extends over a 180 degree arc to directly engage the shoulders of the pair of flexible extension arms allowing said cannula joined to said conical shaped head to be axially rotatable relative to said cylindrical sheath at said locked first position.

* * * * *